(12) United States Patent
Cristiano et al.

(10) Patent No.: US 9,975,832 B2
(45) Date of Patent: May 22, 2018

(54) PROCESS FOR THE PREPARATION OF OSPEMIFENE AND FISPEMIFENE

(71) Applicant: OLON S.P.A., Rodano (MI) (IT)

(72) Inventors: Tania Cristiano, Rodano (IT); Marco Alpegiani, Rodano (IT)

(73) Assignee: OLON S.P.A., Rodano (IT)

( * ) Notice: Subject to any disclaimer, the term of this patent is extended or adjusted under 35 U.S.C. 154(b) by 0 days. days.

(21) Appl. No.: 15/539,695

(22) PCT Filed: Dec. 28, 2015

(86) PCT No.: PCT/IB2015/060007
§ 371 (c)(1),
(2) Date: Jun. 26, 2017

(87) PCT Pub. No.: WO2016/108172
PCT Pub. Date: Jul. 7, 2016

(65) Prior Publication Data
US 2017/0342007 A1     Nov. 30, 2017

(30) Foreign Application Priority Data
Dec. 29, 2014  (IT) .............................. MI2014A2267

(51) Int. Cl.
*C07C 41/16* (2006.01)
*C07C 43/23* (2006.01)

(52) U.S. Cl.
CPC .............. *C07C 41/16* (2013.01); *C07C 43/23* (2013.01)

(58) Field of Classification Search
CPC ................. C07C 41/06; C07C 41/03
See application file for complete search history.

(56) References Cited

U.S. PATENT DOCUMENTS 7,812,197 B2 * 10/2010 Sodervall ................ C07C 41/26
568/641

FOREIGN PATENT DOCUMENTS

| CN | 103242142 A | 8/2013 |
| IN | 2014MU1757 * | 10/2015 |
| WO | 2008099059 A1 | 8/2008 |

OTHER PUBLICATIONS

Grun et al. ("Selective O-alkylation with glycol chlorohydrins via a Mitsunobu reaction. A versatile route to calix[4]- and 1,1'— binaphthocrowns", Tetrahedron, vol. 60, Issue 23, May 2004, pp. 5041-5048).*
Search Report and Written Opinion of PCT/IB2015/060007 dated Apr. 21, 2016.

* cited by examiner

*Primary Examiner* — Rosalynd A Keys
(74) *Attorney, Agent, or Firm* — Silvia Salvadori, P.C.; Silvia Salvadori

(57) ABSTRACT

Disclosed is a process for the synthesis of the active ingredients ospemifene and fispemifene which comprises reacting phenol 4 with an alkylating agent X—$CH_2CH_2$—Y of formula 7, wherein X is a leaving group and Y is the —$(OCH_2CH_2)_n$OH group wherein n is zero or 1; or X and Y, taken together, represent an oxygen atom; to give ospemifene or fispemifene of formula 8.

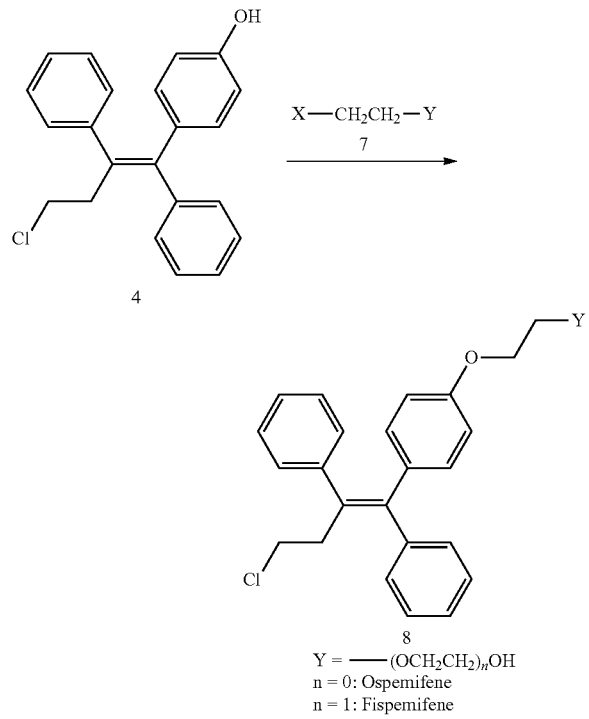

1 Claim, 1 Drawing Sheet

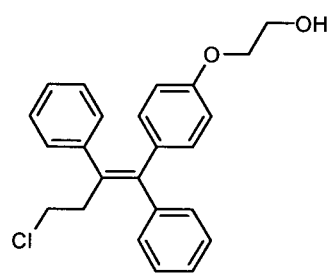
Ospemifene
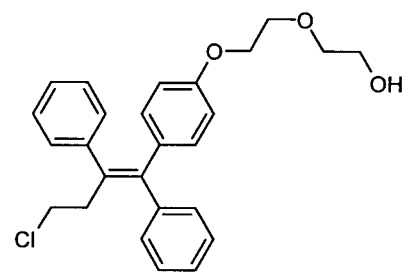
Fispemifene

PROCESS FOR THE PREPARATION OF OSPEMIFENE AND FISPEMIFENE

This application is a U.S. national stage of PCT/IB2015/060007 filed on 28 Dec. 2015, which claims priority to and the benefit of Italian Application No. MI2014A002267 filed on 29 Dec. 2014, the contents of which are incorporated herein by reference in their entireties.

OBJECT OF THE INVENTION

The object of the invention is a process for the preparation of the active ingredients ospemifene and fispemifene.

PRIOR ART

Ospemifene, the chemical name of which is 2-{4-[(1Z)-4-chloro-1,2-diphenyl-1-buten-1-yl]phenoxy}ethanol (FIGURE), is a non-steroidal selective oestrogen-receptor modulator (SERM) which is the active ingredient of a medicament recently approved for the treatment of menopause-induced vulvar and vaginal atrophy.

The preparation of ospemifene, which is disclosed in WO96/07402 and WO97/32574, involves the reaction sequence reported in Scheme 1:

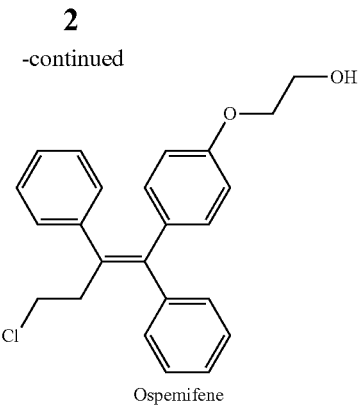

Ospemifene

The first step involves alkylation of 1 with benzyl-(2-bromoethyl)ether under phase-transfer conditions. The resulting product 2 is reacted with triphenylphosphine and carbon tetrachloride to give chloro-derivative 3, from which the benzyl protecting group is removed by hydrogenolysis to give ospemifene.

A more direct method of preparing ospemifene is disclosed in WO2008/099059 and illustrated in Scheme 2.

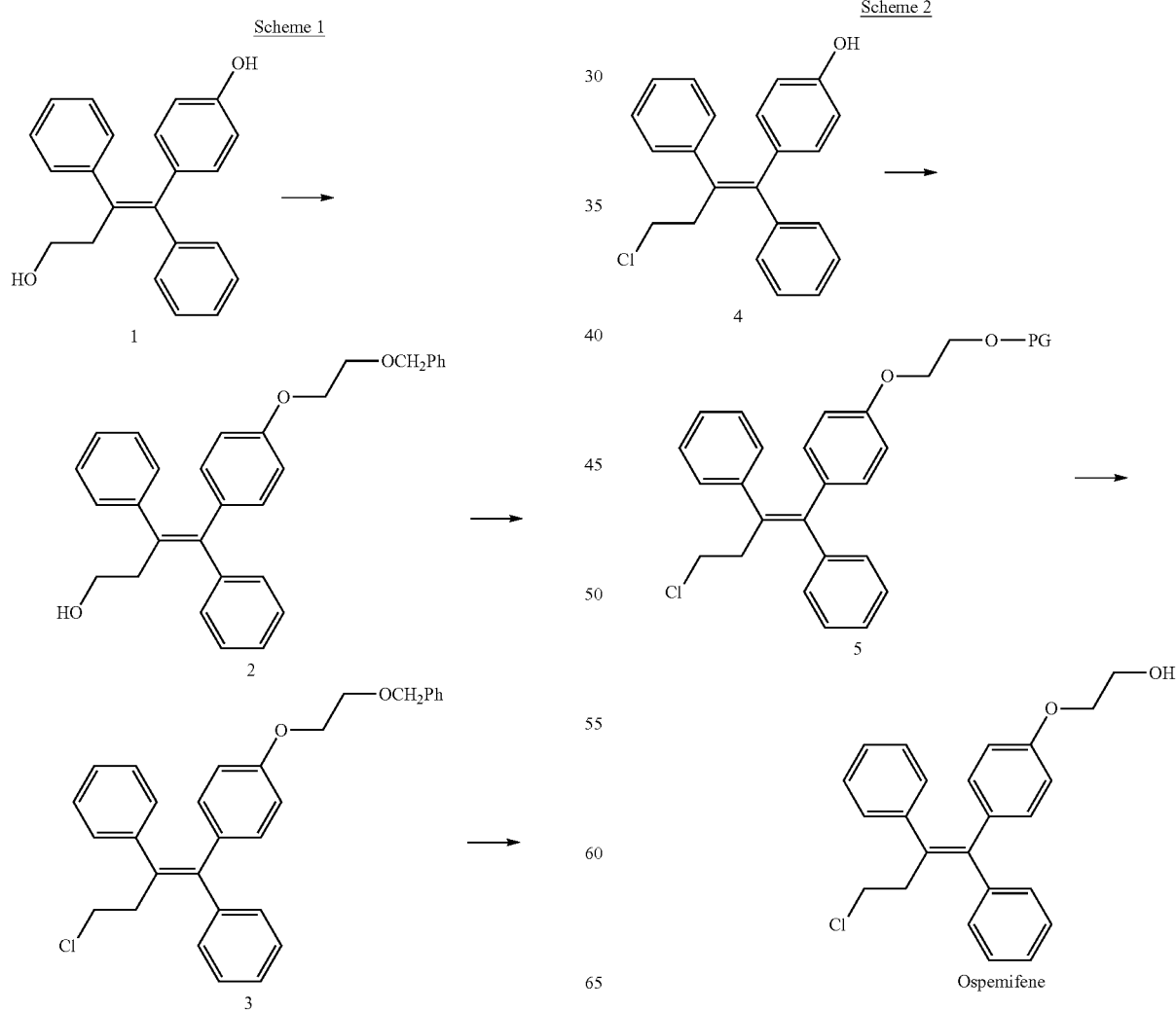

Intermediate 5 (PG=protecting group) is obtained by alkylating 4 with a compound X—CH$_2$—CH$_2$—O-PG, wherein PG is a hydroxy protecting group and X is a leaving group (specifically chlorine, bromine, iodine, mesyloxy or tosyloxy), and then converted to ospemifene by removing the protecting group.

Alternatively (WO2008/099059), phenol 4 is alkylated with a compound of formula X—CH$_2$—COO—R wherein X is a leaving group and R is an alkyl, to give a compound of formula 6, the ester group of which is then reduced to give ospemifene (Scheme 3)

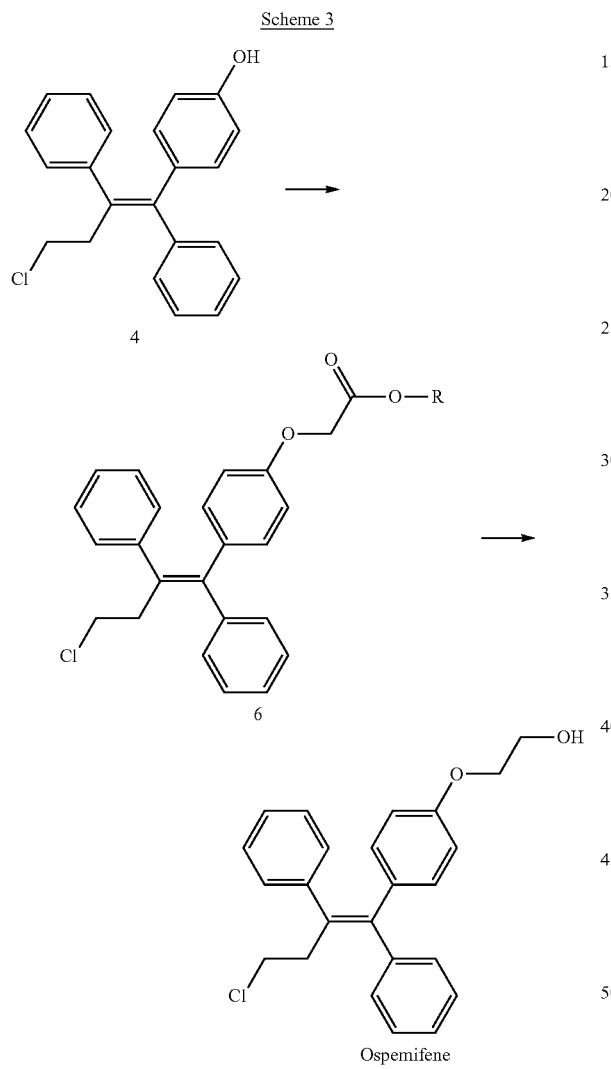

Processes for the synthesis of ospemifene not correlated with those reported in schemes 2 and 3 are also disclosed in the following documents: CN104030896, WO2014/060640, WO2014/060639, CN103242142 and WO2011/089385.

Fispemifene, the chemical name of which is (Z)-2[2-[4-(4-chloro-1,2-diphenylbut-1-enyl)phenoxy]ethoxy]ethanol (FIGURE) is a non-steroidal selective oestrogen-receptor modulator (SERM), initially disclosed in WO01/36360. Publications WO2004/108645 and WO2006/024689 suggest the use of the product in the treatment and prevention of symptoms related with male androgen deficiency. The product is at the clinical trial stage for the treatment of male neurological disorders.

According to an evaluation of the synthesis routes for ospemifene and fispemifene described in the literature, those which use compound 4 (Schemes 2 and 3) are particularly interesting, as 4 is also a key intermediate in the synthesis of toremifene, an oestrogen-receptor antagonist (ITMI20050278).

DESCRIPTION OF FIGURE

FIGURE: Structural formulas of ospemifene and fispemifene

DESCRIPTION OF THE INVENTION

We have surprisingly found that ospemifene and fispemifene can be advantageously synthesised by alkylating phenol 4 with an alkylating agent of formula 7

$$X—CH_2CH_2—Y \qquad 7$$

wherein X is a leaving group and Y is the —(OCH$_2$CH$_2$)$_n$OH group wherein n is zero or 1; or X and Y, taken together, represent an oxygen atom;

to give a compound of formula 8

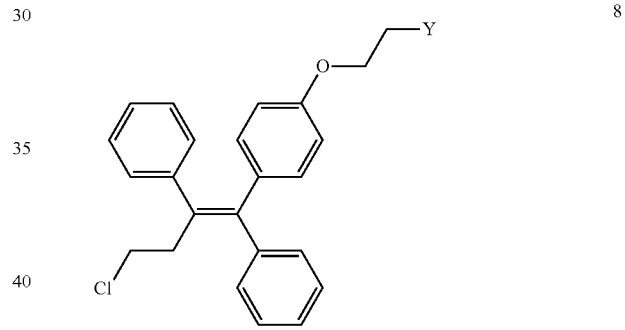

wherein Y is as defined above.

When Y is —(OCH$_2$CH$_2$)$_n$OH wherein n is zero, formula 8 represents ospemifene.

When Y is —(OCH$_2$CH$_2$)$_n$OH wherein n is 1, formula 8 represents fispemifene.

Phenol 4 can therefore be alkylated according to the present invention with no need for protection and subsequent deprotection of the hydroxyl function present in the alkylating reagent.

DETAILED DESCRIPTION OF THE INVENTION

Leaving group X of the compound of formula 7 is preferably a halogen, such as chlorine, bromine or iodine, or an alkyl or arylsulphonate such as mesyloxy or tosyloxy.

In one embodiment of the invention, in the compound of formula 7, X is a leaving group as defined above and Y is —(OCH$_2$CH$_2$)$_n$OH wherein n is zero, and the reaction of 7 with 4 provides ospemifene, as reported in Scheme 4.

Scheme 4

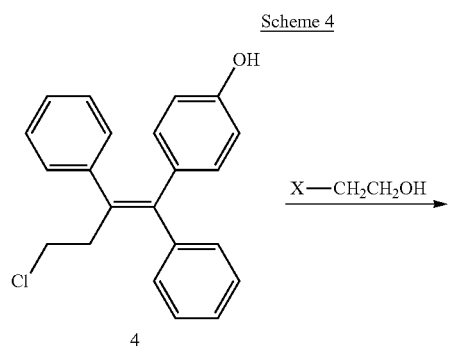

In another embodiment of the invention, in the compound of formula 7, X and Y, taken together, represent an oxygen atom, the compound of formula 7 is ethylene oxide, and the reaction of 7 with 4 provides ospemifene, as reported in Scheme 5.

Scheme 5

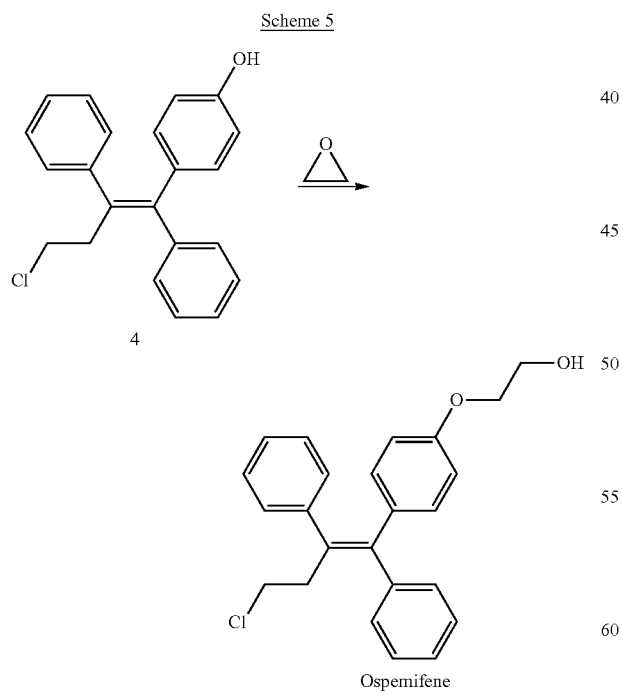

In another embodiment of the invention, X is a leaving group as defined above and n is 1, and the reaction of 7 with 4 provides fispemifene, as reported in Scheme 6.

Scheme 6

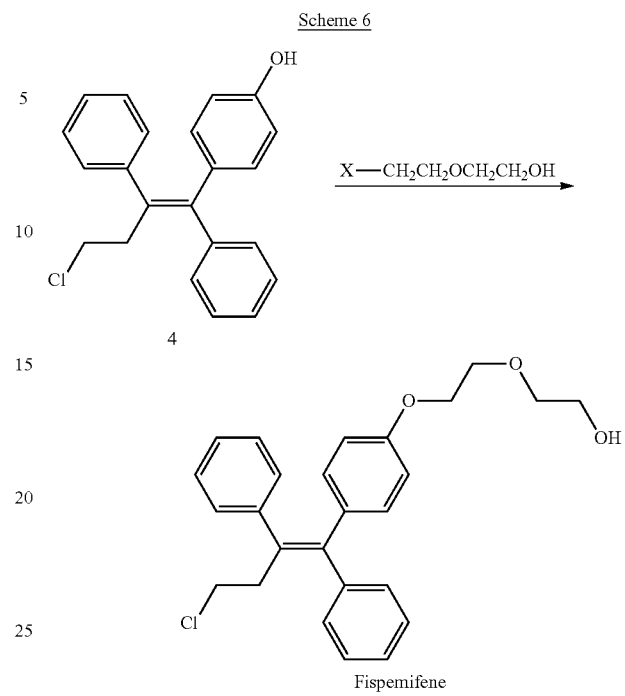

The reaction between phenol 4 and alkylating reagent 7, wherein X is a leaving group as defined above and Y is the —(OCH$_2$CH$_2$)$_n$OH group as defined above, can be effected in an aprotic solvent preferably selected from ethers such as tetrahydrofuran, dioxane, dimethoxyethane, tert-butyl methyl ether, amides such as N,N-dimethylformamide, N,N-dimethylacetamide and N-methylpyrrolidone, nitriles such as acetonitrile, and hydrocarbons such as toluene and xylene, in the presence of a base preferably selected from alkoxides, amides, carbonates, oxides or hydrides of an alkali or alkaline-earth metal, such as potassium tert-butoxide, lithium bis-trimethylsilylamide, caesium and potassium carbonate, calcium oxide and sodium hydride.

The reaction can involve the formation in situ of an alkali or alkaline earth salt of phenol 4, or said salt can be isolated and then reacted with alkylating reagent 7. Examples of phenol 4 salts which can be conveniently isolated are the sodium salt and the potassium salt. Said salts can be prepared by known methods, for example by treatment with the corresponding hydroxides (see preparation of the potassium salt of phenol 4 by treatment with aqueous potassium hydroxide as described in document ITMI20050278), or from the corresponding alkoxides, such as sodium methylate in methanol for the preparation of the sodium salt of phenol 4, as described in the examples of the present application.

Other salts of phenol 4 which can be prepared in situ or isolated for use in the alkylation reaction are quaternary ammonium salts, preferably tetrabutyl-ammonium salt.

The reaction between phenol 4 and alkylating reagent 7, wherein X is a leaving group as defined above and Y is the —(OCH$_2$CH$_2$)$_n$OH group as defined above, can also be effected in a biphasic liquid-liquid system comprising an organic solvent immiscible with water and an aqueous solution of an inorganic base such as an alkali or alkaline earth hydroxide or carbonate, for example the biphasic system consisting of toluene and an aqueous solution of potassium hydroxide.

The reaction can also be carried out in a biphasic solid-liquid system comprising an organic solvent such as an aromatic hydrocarbon like toluene or a chlorinated solvent like methylene chloride, an inorganic base as defined above, such as potassium carbonate, and a catalyst among those commonly used for reactions under phase-transfer conditions, such as a quaternary ammonium salt like tetrabutylammonium bromide, benzyltriethylammonium chloride and similar salts.

The reaction between phenol 4 and ethylene oxide (consisting of formula 7 wherein X and Y, taken together, represent an oxygen atom) can be effected in protic or aprotic solvent in the presence of acid or basic catalysis or can be catalysed by quaternary ammonium or phosphonium salts.

The reactions are carried out for a time and at a temperature sufficient to obtain the desired product. The most effective reaction conditions to optimise the yield and purity of the products obtained can easily be identified by a skilled person.

The products of formula 4 and formula 7 are known products.

The invention will now be illustrated by the following examples.

EXAMPLE 1

Sodium hydride (4.2 g) is loaded in portions into a solution of 4-(4-chloro-1,2-diphenyl-buten-1-yl)phenol (10 g) in tetrahydrofuran (120 ml) in an inert gas environment, and the mixture is maintained under stirring at room temperature for 1 h. 2-Iodoethanol (11 ml) is added dropwise, and the reaction mixture is refluxed for about 9 h. Water is added, and the mixture is concentrated and extracted with ethyl acetate. The organic phase is washed with sodium carbonate aqueous solution and then with water, and then concentrated under vacuum. After crystallisation of the residue from methanol-water (about 5:1), 9.9 g of crude ospemifene is obtained.

EXAMPLE 2

A solution of sodium methylate in methanol (6.25 ml) is added to a solution of 4-(4-chloro-1,2-diphenyl-buten-1-yl) phenol (10 g) in methanol (100 ml) in an inert gas environment, and maintained under stirring at room temperature for 1 h. The mixture is concentrated under vacuum and taken up with tetrahydrofuran (100 ml). A solution of 2-iodoethanol (3.5 ml) in tetrahydrofuran (30 ml) is added dropwise, and the reaction mixture is refluxed for about 3 h. Water is added, and the mixture is concentrated and extracted with ethyl acetate. The organic phase is washed with a saturated sodium hydrogen carbonate aqueous solution, and finally with water. The resulting solution is then concentrated under vacuum and crystallised from methanol-water to obtain 5.8 g of crude ospemifene.

EXAMPLE 3

Potassium tert-butylate (2.0 g) is added to a solution of 4-(4-chloro-1,2-diphenyl-buten-1-yl)phenol (5 g) in tert-butanol (75 ml) in an inert gas environment, and maintained under stirring at room temperature for 1 h. The solvents are concentrated under vacuum, and the concentrate is taken up with tetrahydrofuran (50 ml). A solution of 2-iodoethanol (1.7 ml) in tetrahydrofuran (15 ml) is added in about 30 minutes, and the reaction mixture is then refluxed for about 2 h. The process then continues as described in Example 1, and 2.9 g of crude ospemifene is obtained.

EXAMPLE 4

A 50% potassium hydroxide aqueous solution (4.4 ml) is added to a solution of 4-(4-chloro-1,2-diphenyl-buten-1-yl) phenol (2 g) in toluene (20 ml) in an inert gas environment, and maintained under stirring at room temperature for 15 minutes. 2-Iodoethanol (2.2 ml) is added in about 30 minutes, and the reaction mixture is refluxed and maintained at that temperature for about 7 h. After the addition of water, the phases are separated. The organic phase is washed with a saturated sodium hydrogen carbonate aqueous solution, and finally with water. The organic phase is then concentrated under vacuum. After crystallisation of the residue from methanol-water (about 5:1), 0.85 g of crude ospemifene is obtained.

The invention claimed is:

1. Process for the preparation of ospemifene comprising reacting a compound of formula 4

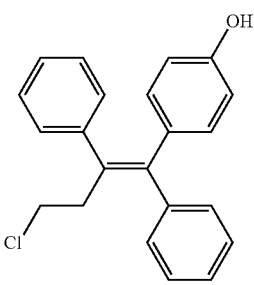

4 with a compound of formula 7

$X—CH_2CH_2—Y$       7 wherein X and Y taken together is an oxygen atom; to give a compound of formula 8

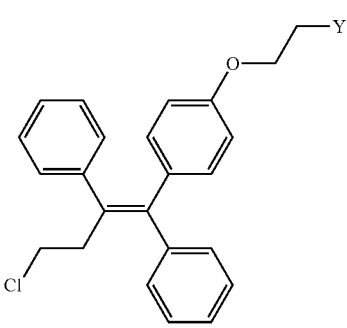

8 wherein Y is OH.

* * * * *